US00PP25926P2

(12) United States Plant Patent
Ault

(10) Patent No.: US PP25,926 P2
(45) Date of Patent: Sep. 22, 2015

(54) ***BAPTISIA* PLANT NAMED 'SANDSTORM'**

(50) Latin Name: ***Baptisia* hybrid**
Varietal Denomination: Sandstorm

(71) Applicant: James Robert Ault, Libertyville, IL (US)

(72) Inventor: James Robert Ault, Libertyville, IL (US)

(73) Assignee: CHICAGOLAND GROWS, INC, Glencoe, IL (US)

( * ) Notice: Subject to any disclaimer, the term of this patent is extended or adjusted under 35 U.S.C. 154(b) by 58 days.

(21) Appl. No.: 13/999,513

(22) Filed: Mar. 5, 2014

(51) Int. Cl.
*A01H 5/00* (2006.01)

(52) U.S. Cl.
USPC ..... Plt./263.1

(58) Field of Classification Search
USPC ..... Plt./263.1, 226
See application file for complete search history.

*Primary Examiner* — Annette Para
(74) *Attorney, Agent, or Firm* — Penny J. Aguirre

(57) ABSTRACT

A new cultivar of interspecific *Baptisia,* 'Sandstorm', that is characterized by its distinctly vase-shaped plant habit with strongly upright stems during anthesis that expand into a broad rounded mound at maximum vegetative growth, its flowers that are bicolored; light yellow-green and suffused with medium to dark violet with lateral petals that are distinctly bicolored with yellow on the lower portion and yellow suffused with medium to dark violet on the upper portion, and its flowers that are uniform, densely borne, and arranged radially on the inflorescences.

2 Drawing Sheets

Botanical classification: *Baptisia* hybrid.
Cultivar designation: 'Sandstorm'.

BACKGROUND OF THE INVENTION

The present invention relates to a new and distinct cultivar of hybrid *Baptisia* plant, botanically known as *Baptisia* 'Sandstorm' and will be referred to hereafter by its cultivar name, 'Sandstorm'. The new cultivar represents a new false indigo, an herbaceous perennial grown for landscape use.

The new invention arose from an ongoing breeding program in a dedicated test plot in Glencoe, Ill. The objective of the breeding program is to develop novel interspecific hybrids of *Baptisia* that exhibit unique flower coloration, hybrid vigor, ease of clonal propagation, and desirable plant habits.

'Sandstorm' was selected as a single unique plant by the Inventor in June of 2007 after evaluating seedlings that derived from a cross made in May of 2002. The female parent was an unnamed plant from the Inventor's breeding program that derived from open pollination of an interspecific hybrid *Baptisia* (*australis*×*leucophaea*). The male parent was *Baptisia*×*bicolor* 'Starlite' (U.S. Plant Pat. No. 19,971).

Asexual propagation of the new cultivar was first accomplished by shoot tip cuttings in July of 2009 in Glencoe, Ill. under the direction of the Inventor. Asexual propagation by shoot tip cuttings has determined that the characteristics of the new cultivar are stable and are reproduced true to type in successive generations.

SUMMARY OF THE INVENTION

The following traits have been repeatedly observed and represent the characteristics of the new cultivar as observed in Glencoe, Ill. These attributes in combination distinguish 'Sandstorm' as a unique cultivar of *Baptisia.*

1. 'Sandstorm' exhibits a distinctly vase-shaped plant habit with strongly upright stems during anthesis that expand into a broad rounded mound at maximum vegetative growth.
2. 'Sandstorm' exhibits flowers that are bicolored; light yellow-green and suffused with medium to dark violet with lateral petals that are distinctly bicolored with yellow on the lower portion and yellow suffused with medium to dark violet on the upper portion.
3. 'Sandstorm' exhibits flowers that are uniform, densely borne, and arranged radially on the inflorescences.

The female parent of 'Sandstorm' differs from 'Sandstorm' in having flowers that are lavender to blue in color with a yellow keel and in having inflorescences that are mostly hidden in the foliage. 'Starlite', the male parent of 'Sandstorm' differs from 'Sandstorm' in having flowers that are lavender to blue in color with a yellow keel, in having an earlier bloom period, and in having inflorescences that are longer in length (and average of 60 cm). 'Sandstorm' can be most closely compared to typical plants of *Baptisia leucophaea* and to the *Baptisia* cultivar 'Twilite' (U.S. Plant Pat. No. 19,011). Typical plants of *Baptisia leucophaea* differ from 'Sandstorm' in having flowers that are cream in color with hints of lemon yellow, in having horizontal inflorescences, in having secund inflorescences, and in having an early bloom period. 'Twilite' differs from 'Sandstorm' in having flowers that are mainly violet purple in color with yellow keels, in having a later starting bloom period, in being larger in overall plant size, and in having foliage that is medium yellow-green in color.

BRIEF DESCRIPTION OF THE DRAWINGS

The accompanying colored photographs illustrate the overall appearance and distinct characteristics of the new *Baptisia.* The photographs in FIG. 1 and FIG. 2 were taken of plants seven years in age and the photograph in FIG. 3 was taken of a plant 11 years in age. Plants were grown outdoors in a trial plot in Glencoe, Ill.

The photograph in FIG. 1 provides a close up view of an inflorescence of 'Sandstorm'.

Figure 1:
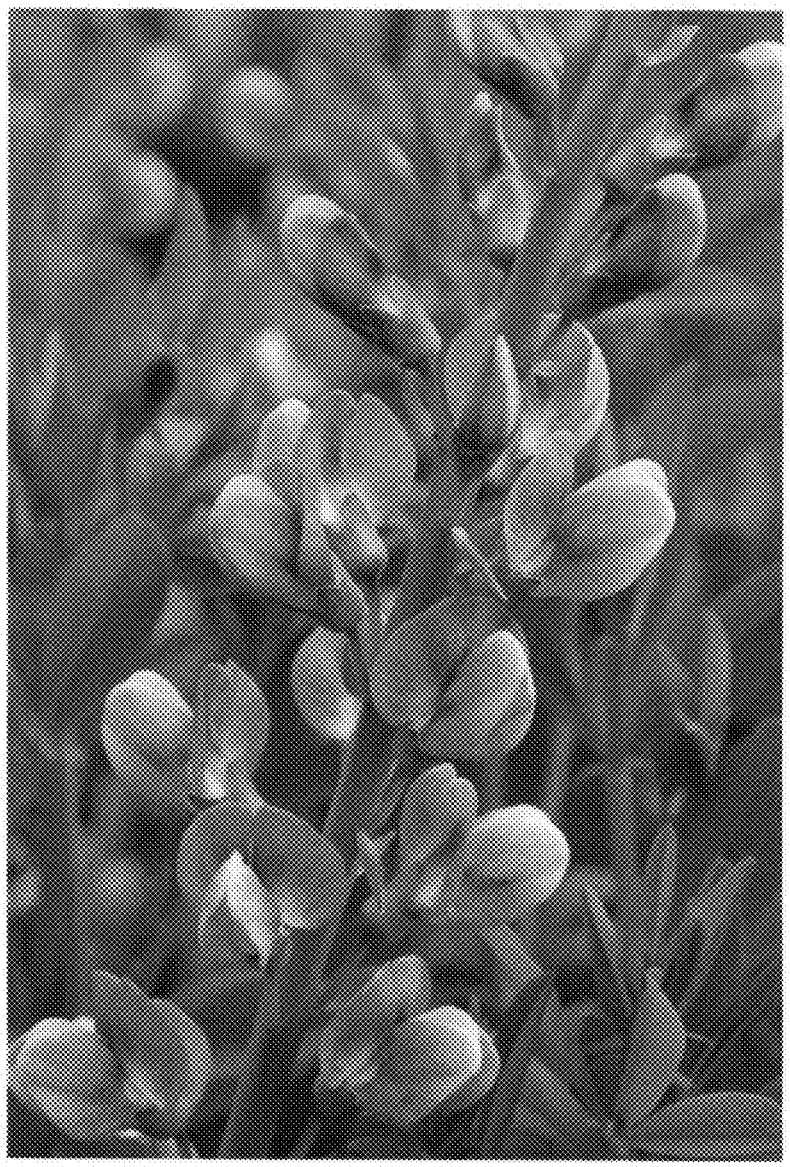
Figure 2:
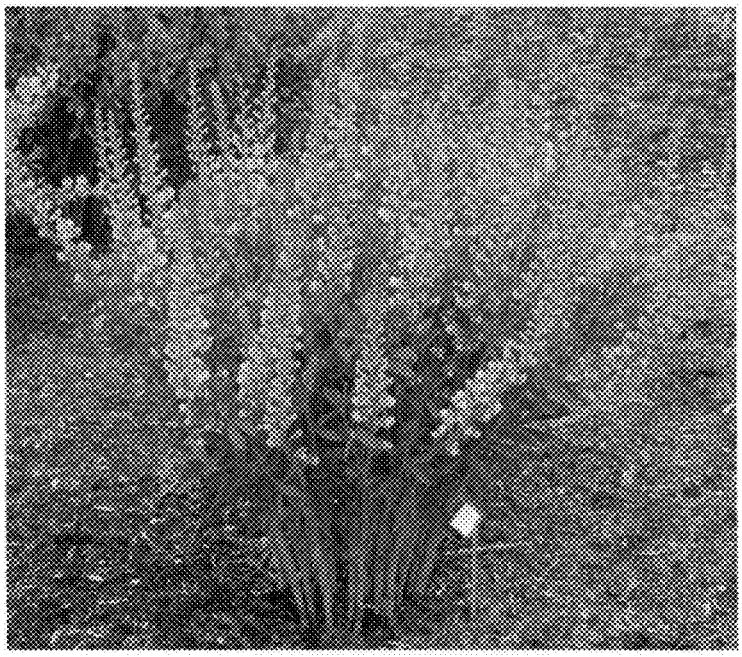

The photograph in FIG. 2 is a side view of 'Sandstorm' in bloom and illustrates the vase-shaped flowering plant habit.

Figure 3:
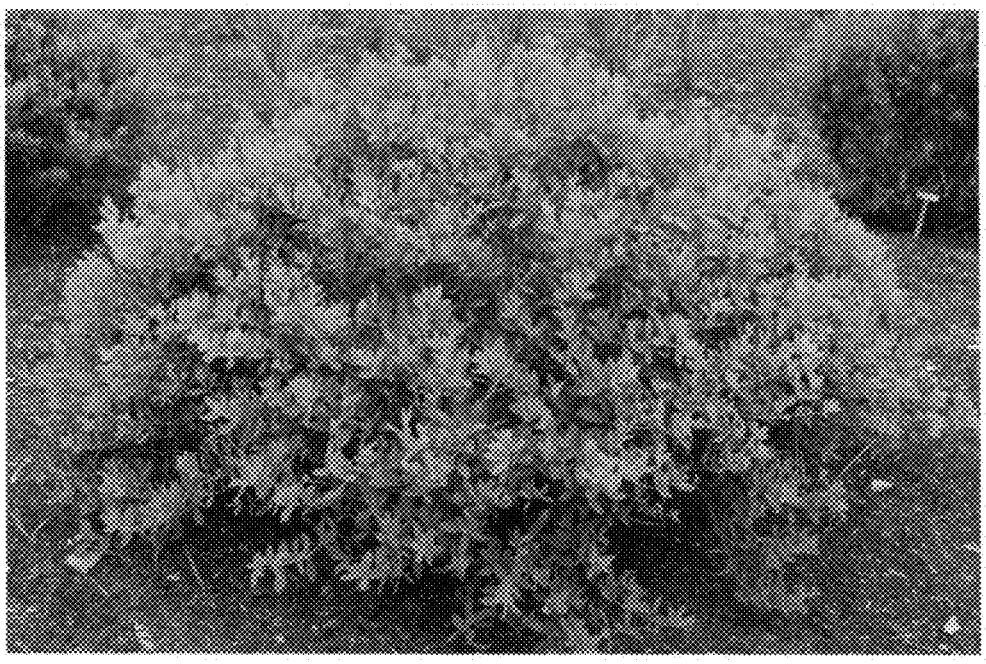

The photograph in FIG. 3 provides a side view of the broad, rounded, post bloom foliage of a plant of 'Sandstorm'.

The colors in the photographs are as close as possible with the photographic and printing technology utilized and the color values cited in the detailed botanical description accurately describe the colors of the new *Baptisia*.

DETAILED BOTANICAL DESCRIPTION OF THE PLANT

The following is a detailed description of eight year-old plants of the new cultivar as grown outdoors in a trial plot in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Three to four weeks from mid-May to early to mid-June in northern Illinois (USDA Zone 5).

*Plant habit*.—Distinctly vase-shaped in bloom, becoming a broad rounded mound at maximum vegetative growth.

*Height and spread*.—An eight year old plant attains a height of 1.1 m and a width of 1.5 m (vegetative growth), a ten year-old plant reaches a spread of 2.2 m (vegetative growth).

*Hardiness*.—U.S.D.A. Zones 4 to 7.

*Culture*.—Prefers well-drained to medium moist soils in full sun, tolerant to lean soils, some stems may lodge in severe drought.

*Diseases*.—Some leaf spot observed during severe summer drought.

*Root description*.—Deep rooted, fibrous.

*Propagation*.—Shoot tip cuttings.

*Growth rate*.—Vigorous.

Stem description:

*Branch habit*.—Densely branched; average of 33 branches, each with an average of 3 secondary branches, and 2 tertiary branches.

*Stem size*.—Main stem; average of 95 cm (including peduncle) in length and 9 mm in width, secondary; average of 30 cm in length and 3 mm, tertiary; an average of 9 cm in length and 2 mm in width.

*Stem shape*.—Oval.

*Stem color*.—144A.

*Stem surface*.—Glabrous, satiny but slightly glaucous with ridges.

Foliage description:

*Leaf shape*.—Fan-shaped in overall outline.

*Leaf division*.—3-palmate.

*Leaf internode*.—Foliage begins 18 cm from base until foliage expands, an average of 7 cm on main stem and an average of 5 cm on secondary branches.

*Leaf size*.—Average 5 cm in length and 5.5 cm in width when mature.

*Leaf quantity*.—About 16 per stem.

*Leaflet shape*.—Oblanceolate.

*Leaflet base*.—Acuminate.

*Leaflet apex*.—Acute.

*Leaflet venation*.—Pinnate pattern, not conspicuous, color matches leaflet color on the upper and lower surface with the mid rib of lower surface 138C.

*Leaflet margins*.—Entire.

*Leaf attachment*.—Petiolate.

*Leaf arrangement*.—Alternate.

*Leaflet surface*.—Glabrous and slightly glaucous on upper and lower surface.

*Leaflet color*.—Newly expanded; upper and lower surface 137A, mature; upper and lower surface 137B.

*Leaflet size*.—An average of 5.1 cm in length and 1.3 cm in width.

*Petioles*.—Average of 6 mm in length and 2 mm in width, clasping to stem at mature nodes, 144B in color, surface is glabrous and satiny.

*Stipules*.—Lanceolate in shape, base is truncate to stem, apex is narrowly acute to acuminate, up to 3.5 cm in length and 1 cm in width on mature leaves, 138A in color on upper and lower surface.

Flower description:

*Inflorescence type*.—Terminal racemes of pea-like flowers on main and secondary branches, blooms from the base to the apex.

*Inflorescence size*.—Average of 39 cm in length and 5 cm in width in mid section.

*Lastingness of inflorescence*.—About 20 days.

*Flower size*.—About 2.4 cm in depth and about 1.6 cm in diameter.

*Flower fragrance*.—Faint.

*Flower number per inflorescence*.—About 60.

*Peduncle*.—Oval in shape, up to 48 cm in length and an average of 5 mm in width, 144A in color, surface is glabrous, satiny and slightly glaucous with ridges, flower internode length averages 1.2 cm.

*Petiole*.—About 5 mm in length, about 1 mm in width, oval in shape, 138A in color, glabrous and satiny surface.

*Flower buds*.—Kidney-shaped, about 2 cm in length and 0.9 mm in width, petal portion is 1C with a slightly flush of N88C, calyx portion same as open flowers.

*Flower type*.—Papilionaceous, held at about a 45° angle.

*Calyx*.—Campanulate, about 9 mm in length and 7 mm in diameter, surface is glabrous and satiny, 138B in color, persistent.

*Sepals*.—5, fused with the exception of apex of each, free portion is triangular in shape, 3 mm in width and depth with an acute apex, color 138B, surface is glabrous on both surfaces.

*Corolla features*.—Papilionaceous (4 segments) with a moderately reflexed banner, 2 lateral wings and a concealed keel, lateral wings; oblong in shape, about 2 cm in length and 9 mm in width, color on outer surface and the inner surface on the lower portion is 1C and on the upper portion 1C and lightly suffused with 86A and changing to 1C and slightly suffused with N88C, rounded apex, oblique base keel; not visible visible, comprised of 2 segments surrounding reproductive organs, oblong (slightly oblique) in shape with rounded apex and oblique base, 1.7 cm in length and 9 mm in width, upper surface and lower surface are 1C in color, segments joined at center point, banner; orbicular in shape, about 1.8 cm in length and 1.7 cm in width, color on outer surface and the inner surface is 1C and lightly suffused with 86A and changing to 1C and slightly suffused with N88C, apex is rounded with a single notch, surface is glabrous on all sections.

*Receptacle*.—Disk-shaped, gelatinous, 137B in color, about 2 mm in diameter and 1.5 mm in depth.

Reproductive organs:

*Gynoecium*.—1 Pistil, about 2.2 cm in length, 1.5 mm in width; style is 144B in color and 1.1 cm in length; stigma minute, too small to read color, ovary is superior with a stipe, 144A in color, 1 cm in length and 2 mm in width; stipe is 144B in color, 3 mm in length and 1 mm in width.

*Androcoecium*.—10 stamens, not united, 2 cm in length and 1 mm in width; filament is 1.9 cm in length, 1 mm in width and 145B in color; anther is dorsifixed, 1.5 mm in length and 1 mm in width and 165B in color, pollen is moderate in quantity and 14B in color.

*Fruit*.—An inflated pod, technically a legume, average of 2 produced per inflorescence (open-pollinated), elliptic and slightly oblong in shape, average of 2.5 cm in length by 1.8 cm in width with a beak approx. 5 mm in length, color of outer surface and inner surface when mature is 202A, walls 1.5 mm and hard at maturity, seed; average of 6 per fruit (open-pollinated), 160B in color, oval with the hilum side more or less straight, seed compressed to flattish, 5 mm in length, 4 mm in width and 2 mm in thickness.

It is claimed:

1. A new and distinct cultivar of *Baptisia* plant named 'Sandstorm' as herein illustrated and described.

* * * * *